US00PP31248P2

(12) United States Plant Patent
Hansen

(10) Patent No.: US PP31,248 P2
(45) Date of Patent: Dec. 17, 2019

(54) **X *MANGAVE* PLANT NAMED 'THUNDERBIRD'**

(50) Latin Name: **x *Mangave* hybrid**
Varietal Denomination: Thunderbird

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/501,207

(22) Filed: Mar. 6, 2019

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden

(57) ABSTRACT

A new and unique x *Mangave* plant named 'Thunderbird' characterized by a rounded mound of fleshy, short, fleshy, slightly cupped, gladiate to lanceolate leaves that develop densely concentrated reddish mottling with intense light. The leaves are predominately upwardly pointing in center portion of the plant and outwardly and curving upwardly in the outer portion of plant. The leaves have numerous small, firm marginal teeth and small, sharp, apical mucro. The new plant is suitable for the garden or as a potted plant in the garden or home.

2 Drawing Sheets

Botanical classification: x *Mangave* hybrid.
Variety denomination: 'Thunderbird'.

STATEMENT REGARDING PRIOR DISCLOSURES UNDER 37 CFR 1.77(B)(6)

The first public disclosure of the claimed plant, in the form of a private sale, was made by Walters Gardens, Inc. on Mar. 12, 2018 to Plant Delights Nursery, Inc. Plants for this sale were obtained from the inventor. No plants of x *Mangave* 'Thunderbird' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Thunderbird' that was hybridized by the inventor at a wholesale perennial nursery in Zeeland, Mich., USA as a cross between a proprietary unnamed x *Mangave* hybrid known only as 12-41-5 (not patented) as the female or seed parent times a proprietary selection of *Manfreda virginica* named AL-55 (not patented) as the male or pollen parent. The cross was performed Oct. 13, 2014 and seeds were harvested and sown early winter of 2015. Through trials at the same nursery the plant was assigned the breeder code 15-4-3. The new plant has been successfully asexually propagated by sterile shoot-tip tissue culture and by basal offsets at the same nursery in Zeeland, Mich. The asexual tissue culture propagation has been found to produce stable and identical plants that maintain all the unique characteristics of the original plant.

BRIEF SUMMARY OF THE INVENTION x *Mangave* 'Thunderbird' differs from its parents as well as all other *Manfreda, Agave* and x *Mangave* known to the applicant. The female parent has leaves that are more sinuate, broader, longer, with fewer leaves per plant, with larger marginal teeth, and distinctly spotted in burgundy with less overlapping under strong ultraviolet light conditions. The male parent has narrower, fleshier foliage that lacks marginal teeth and apical spines, has reddish spotting at the base of the leaves in high ultraviolet light, and the habit is flatter with fewer leaves per plant. The nearest comparison plants are: 'Blazing Saddles' copending U.S. Plant Patent Application, 'Mission to Mars' U.S. Plant Pat. No. 29,393 and 'Red Wing' U.S. Plant patent application Ser. No. 16/350,922. 'Blazing Saddles' has more outwardly pointing foliage with smaller, more flexible and more numerous teeth. 'Red Wing' has more leaves per plant that are more outwardly pointing, with smaller marginal teeth and more uniform reddish coloration in high ultraviolet light. 'Red Wing' also is slower to reach flowering maturity. 'Mission to Mars' has a larger habit with larger, broader foliage and taller flower spikes.

'Thunderbird' is unique from all of the above cultivars and all *Agave*, x *Mangave* and *Manfreda* known to the inventor by the following combined traits:

1. Upright mound of gladiate to lanceolate, short, sarcous leaves;
2. Leaves develop dense mottled reddish to greyed reddish-purple spotting with strong ultraviolet light;
3. Leaf margins have small, firm, marginal teeth that develop a deep burgundy coloration;
4. Moderate growth rate;
5. Foliage is upright with outer leaves slightly outwardly and arching upwardly toward apices.

BRIEF DESCRIPTION OF THE DRAWING

The photograph of x *Mangave* 'Thunderbird' demonstrates the overall appearance of the new plant including the unique traits as three-year-old plants grown in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
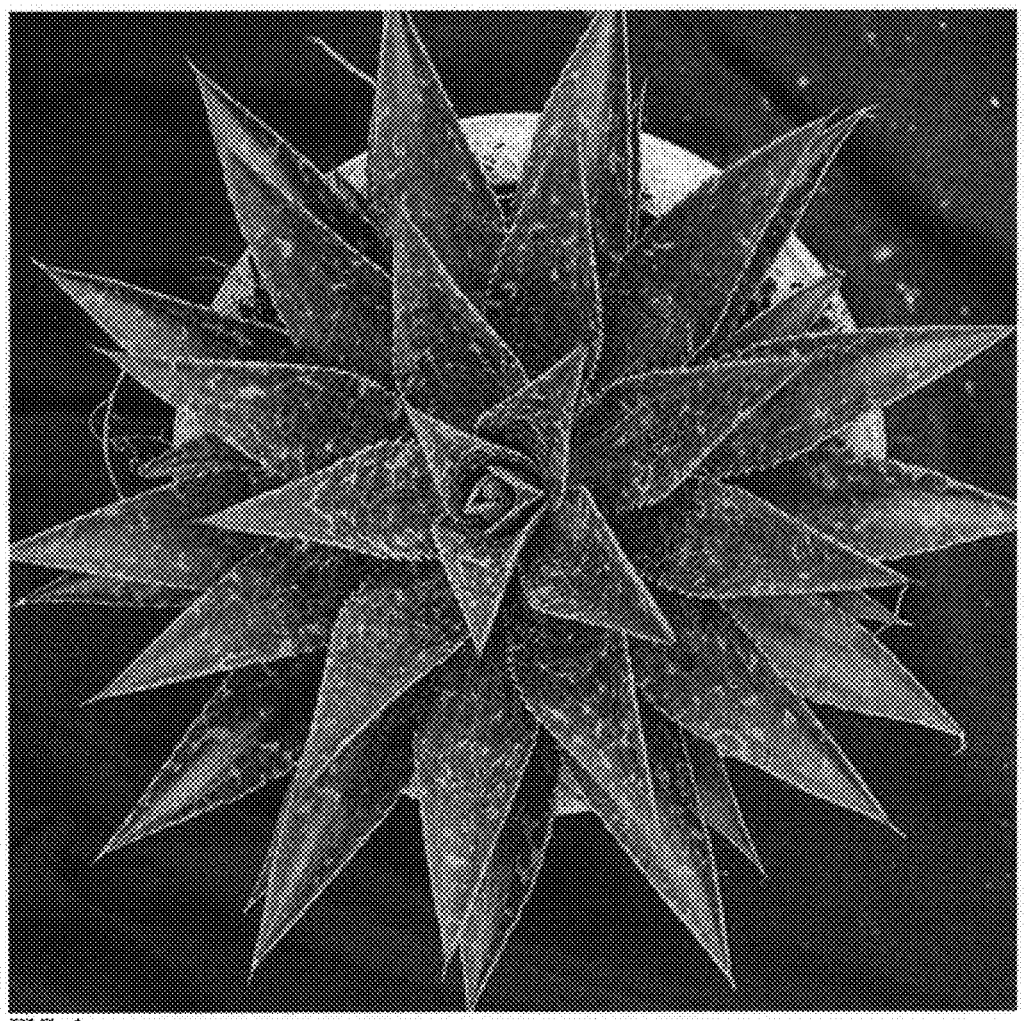
FIG. 1 shows a new plant from above grown in full-sun.
Figure 2:
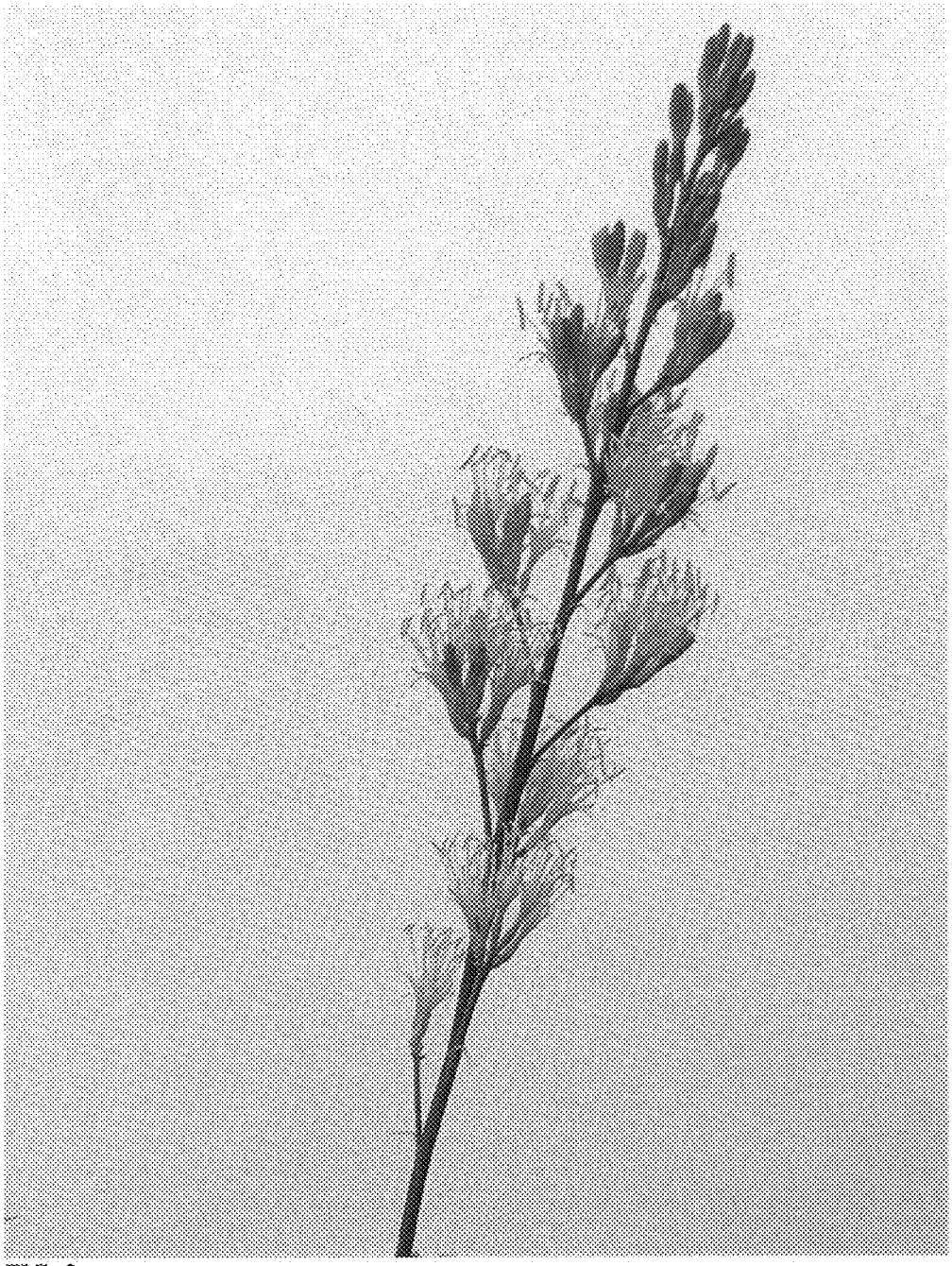
FIG. 2 shows the upper flowering portion of the new plant.

The following descriptions and color references are based on the 2015 edition of The Royal Horticultural Society Colour Chart except where common dictionary terms are used. The new plant, x *Mangave* 'Thunderbird', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse and full-sun trial garden in Zeeland, Mich. with supplemental water and fertilizer as needed.

Parentage: A proprietary unnamed hybrid 12-41-5 as female or seed patent, *Manfreda virginica* AL-55as the male or pollen parent; The female parent is a cross between a proprietary selection of *Manfreda maculosa* (not patented) and a proprietary selection of *Agave marmorata* (not patented).

Propagation: By sterile shoot-tip tissue culture and removal of basal offsets;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 30 cm long;

Root color: Nearest RHS 158C;

Plant shape and habit: Succulent herbaceous perennial with basal rosettes of leaves radially emerging outwardly from central stem, producing a radially-symmetrical, rounded mound;

Plant size: Foliage height about 26.0 cm tall from soil line to the top of the leaves and about 34.0 cm wide at the widest point about middle of the plant;

Stem: To about 6.0 cm across; covered with leaves;

Foliage description: Gladiate to lanceolate; simple; sessile; bi-laterally symmetrical; sarcous; apex narrowly acute with firm terminal spine; base slightly flaring, truncate; slightly concavo-convex; margins flat, finely dentate with small, firm teeth; glabrous abaxial and adaxial; glaucous abaxial and adaxial;

Terminal spine: Firm in maturity; to about 4.0 mm long and 1.0 mm wide at base;

Marginal teeth size: About 1.5 mm long and 2.0 mm wide at base, average spacing about 3.4 mm apart;

Leaf size: To about 20.0 cm long, about 40.0 mm wide toward middle, narrowing to about 30.0 mm before flaring at base to 45.0 mm wide; center base about 10.0 mm thick at basal midrib; average about 18.0 cm long, 33.0 mm wide and 9.0 mm thick in longitudinal center; spots on both adaxial and abaxial frequently overlapping to cover nearly all of both surfaces with high intensity ultraviolet light, size of spots indistinct;

Foliage fragrance: None observed;

Leaf number: About 70 per plant;

Leaf blade color:

*Adaxial* (*low ultraviolet light exposure*).—Variable, nearest RHS 138A and RHS 146C with spots between RHS 176B and RHS 176C.

*Abaxial* (*low ultraviolet light exposure*).—Variable, nearest RHS 138A and RHS 146C with spots of nearest RHS 176C.

*Adaxial* (*high ultraviolet light exposure*).—Small greenish patches variable in color from nearest RHS 138B and RHS 146D and dense reddish mottling of nearest RHS 187D and a blend between RHS 187B and RHS N187A.

*Abaxial* (*high ultraviolet light exposure*).—Variable small greenish patches nearest RHS 146D and RHS 138B with reddish portion nearest RHS 187B blended with RHS N187B.

*Teeth*.—Nearest RHS 187A on older leaves, between RHS 155A and RHS 160D on younger leaves.

*Terminal spine*.—Nearest RHS 200B.

Petiole: Leaves sessile;

Veins: Parallel; not distinct abaxial or adaxial;

Peduncle: Terete; glaucous; glabrous; stiff; strong; lightly branched; about 120.0 cm long and 8.0 mm diameter at base and 5.0 mm diameter below first flowers; flowering portion about 50.0 cm tall and about 13.0 cm across; branches to about 6.0 cm long and about 2.5 mm diameter at base; attitude main peduncle and branches upwardly, erect;

Peduncle color: Basal portion before flowers between RHS N187B and RHS 187B; upper flowering portion nearest RHS 137B with blush of nearest RHS 187B;

Pedicel: Terete; glaucous; glabrous; stiff; strong; upwardly; average about 3.0 mm long and 2.2 mm diameter;

Pedicel color: Nearest RHS 138A;

Cauline leaves: About 12 per scape; lanceolate; simple, fleshy, glabrous; margins finely dentate with firm teeth; apex narrowly acute; base truncate, sessile, clasping; proximally about 3.5 cm long and about 6.0 mm wide at base, decreasing distally; color adaxial and abaxial same as basal leaves and depends on ultraviolet light exposure;

Buds one day prior to opening: Elongated globose with acute apex and rounded base; about 3.2 cm long and about 7.0 mm diameter at mid-tepal, base about 4.0 mm diameter;

Bud color: Between RHS 160B and RHS 11B in distal portion and basally nearest RHS 138B;

Flower description: Perfect, actinomorphic; about 5.5 cm long and 3.0 cm wide to exserted anthers, corolla opening to about 3.0 cm across and 3.5 cm tall; lasting about 3 to 4 days per flower; flowering period about three weeks in late winter in greenhouse; producing abundant nectar; approximately 90 flowers per scape; attitude mostly upright;

Flower fragrance: Not detected;

Tepals: Six in two identical sets of three; glaucous abaxial and slightly lustrous adaxial; glabrous both adaxial and abaxial; acute apex and fused base; about 3.4 cm long, fused in basal 2.2 cm and about 4.0 mm wide at base;

Tepal color: Adaxial outer and inner tepal set base nearest RHS 11A; abaxial nearest RHS 18B; Androecium: six;

*Filaments*.—Six; terete distally, slightly applanate base; stiff and straight; about 3.0 cm long and 1.0 mm diameter at base; color nearest RHS 11D.

*Anther*.—Dorsifixed; longitudinal; about 12.0 mm long and 1.5 mm diameter before opening; after dehiscence curving backward slightly; color nearest RHS 19A.

*Pollen*.—Abundant; color nearest RHS 11C.

Gynoecium: Single;

*Style*.—2.5 cm long and 2.0 mm diameter at base; color nearest RHS 11D.

*Stigma*.—Turbinate, apex tri-lobed; about 2.0 mm tall and 2.0 mm across top; color nearest RHS 155A.

*Ovary*.—Inferior; oblong; about 10.0 mm long and 3.5 mm across; nearest RHS 138B.

Fruit and seed not observed;

Disease resistance: X *Mangave* 'Thunderbird' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Thunderbird' as herein described and illustrated.

* * * * *